Figure 1:
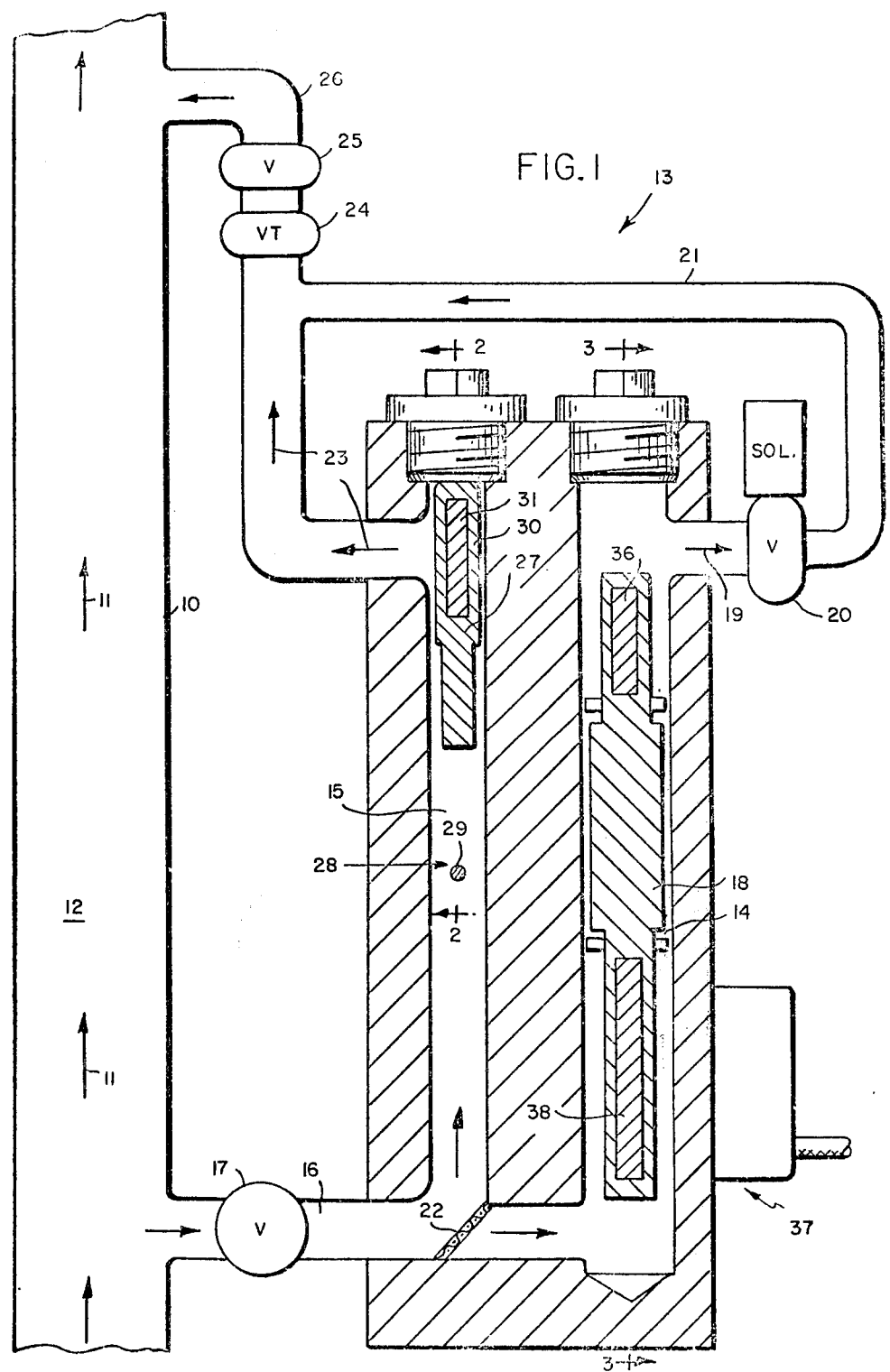

United States Patent [19]

Norcross

[11] 4,154,094

[45] May 15, 1979

[54] FLUID MEASURING APPARATUS

[75] Inventor: Austin S. Norcross, Waban, Mass.

[73] Assignee: Norcross Corporation, Newton, Mass.

[21] Appl. No.: 865,678

[22] Filed: Dec. 29, 1977

[51] Int. Cl.² .......................................... G01N 11/12
[52] U.S. Cl. ...................... 73/57; 210/332; 210/409
[58] Field of Search ............... 73/57; 210/81, 332, 210/409, 433 R

[56] References Cited

U.S. PATENT DOCUMENTS

| | | | |
|---|---|---|---|
| 1,876,439 | 9/1932 | Whaley | 210/409 X |
| 3,304,765 | 2/1967 | Norcross | 73/57 |
| 3,622,004 | 11/1971 | Meyer | 210/409 X |
| 3,686,931 | 8/1972 | Norcross | 73/57 |

FOREIGN PATENT DOCUMENTS

| | | | |
|---|---|---|---|
| 635340 | 11/1963 | Belgium | 73/57 |
| 899369 | 6/1962 | United Kingdom | 73/57 |

*Primary Examiner*—Richard C. Queisser
*Assistant Examiner*—Joseph W. Roskos
*Attorney, Agent, or Firm*—Robert F. O'Connell

[57] ABSTRACT

A fluid handling apparatus, such as a viscometer of the falling piston type, wherein at least a portion of the fluid in a main conduit is diverted into a secondary conduit system which includes a measurement channel having a filter at the entrance to prevent entry of undesired material. When the flow of fluid into the measurement channel is stopped, the fluid flows past the filter, removes the undesired material which has been retained thereat, and carries it back into the main stream. The viscometer can further provide means for producing an external visual indication of the piston movement within the channel. Further, the fluid can be permitted to flow continuously in a second channel, thermally coupled to the measurement channel, so as to maintain the temperature of the measurement channel at or substantially near that of the main stream. Further means can be provided in the second channel to permit adjustment of the fluid flow in the measurement channel to assure adequate operation of the device.

16 Claims, 4 Drawing Figures

FLUID MEASURING APPARATUS

INTRODUCTION

This invention relates generally to improved apparatus for providing a measurement of fluid characteristics and, more particularly, to viscometer apparatus for measuring the viscosity of a fluid using gravity fall techniques.

BACKGROUND OF THE INVENTION

In fluid measuring apparatus where measurements of the characteristics of a fluid are made from a sample of a main stream thereof, a portion of the fluid present in a main conduit is usually diverted therefrom into a secondary conduit where the measurement is to be made. For example, in viscometer apparatus for measuring the viscosity of fluids using gravity fall techniques, as disclosed for example in U.S. Pat. No. 3,686,931, issued to Austin Norcross on Aug. 29, 1972, a portion of the fluid whose viscosity is to be measured is diverted into a second conduit where the viscosity measuring device is placed. The fluid is caused to come to rest within the secondary conduit and a weighted piston is permitted to fall freely under gravity through the fluid within the secondary conduit. The time of such fall over a known distance provides a measurement of the viscosity of the fluid.

Because the clearance between the free falling piston and the walls of the secondary conduit is normally relatively small, it has been found that impurities, such as dirt or other undesired materials suspended therein, often become lodged in such narrow clearance space and adversely affect the velocity of fall and, hence, the accuracy of the viscosity measurement. Moreover, the presence of impurities will adversely affect the operation of valves which are used in the apparatus. It is desirable, therefore, to provide a relatively clear fluid (i.e., a fluid free of such impurities) in which undesired particles, at least above a specified size, are removed from the fluid before it is diverted into the secondary conduit.

While such removal can be effected by placing a screen essentially perpendicular to the fluid flow into the secondary conduit, it is necessary periodically to clean the screen on which the undesired material has collected. In order to do this it is usually necessary to stop the operation of the viscometer and to disassemble the device in order to obtain access to the screen in order to clean and/or replace it. The device must then be reassembled before it can be placed back into operation. Such cleaning and/or replacement procedures can be sufficiently costly and time-consuming so as to make it desirable to provide for such removal in a more effective manner, without requiring the substantial disassembly of the device and the consequent down time which results.

Further, in such measuring systems, in order to assure that the falling piston has reached its desired initial position, a push rod is often utilized for moving the piston within the conduit to such position. The use of external push rods requires the use of a stuffing box which creates troublesome maintenance problems which it is desirable to avoid. On the other hand, if the piston is permitted to rise to its initial position in the conduit merely by utilizing the pressure introduced by the flow of the fluid into the conduit, it cannot always be assured that the piston has reached its correct initial position, since it is not possible in present-day apparatus of this type to determine the position of the piston within the conduit.

Moreover, in present-day devices the beginning of the free fall time period is normally determined by the closure of a valve, which prevents further entry of fluid into the conduit, and the end of the free fall time period is detected by a proximity circuit which, through appropriate magnets, causes the actuation of an electric circuit for providing a visual indication, such as a light, when the piston reaches its lowest point. Such a proximity detection device is disclosed, for example, in U.S. Pat. No. 3,677,070, issued to Austin Norcross, on July 18, 1972. Since the use of such proximity device adds to the cost of the apparatus, it is desirable to provide for an external indication of the piston position without the need for such a device and thereby reduce the cost while still maintaining adequate accuracy of the viscosity measurement. Such an external indication of the position of the falling piston permits an operator to know at all times the location thereof within the measuring conduit.

Further, in present day devices, when the flow is stopped so that the viscosity measurement can take place, the cessation of flow sometimes causes a sufficient change in fluid temperature to adversely affect the accuracy of the measurement. It is further desirable, therefore, to provide an apparatus in which such temperature changes are minimized.

BRIEF SUMMARY OF THE INVENTION

In order to avoid the aforesaid problems and to achieve improved operation in such devices, the invention provides for a secondary conduit system which comprises two channels, a first measurement channel for use in providing the desired measurement and a second auxiliary channel for use in assisting in the removal of undesired material in the fluid which enters the measurement channel without requiring disassembly of the device. For the purposes of illustration, the system of the invention is described with reference to its particular use in a viscometer of the free-falling piston type, although the basic principle may find use in other devices as would occur to those in the art.

In accordance therewith, a screen is placed at a selected angle with reference to the entrance of the fluid into the measurement channel, the entering fluid passing through such screen while particulate materials greater than a predetermined size are retained at the screen, primarily due to the force of fluid against the screen. A major portion of the fluid which is diverted from the main conduit enters the auxiliary channel while a relatively smaller portion thereof enters the measurement channel, the latter portion thereby causing the piston therein to rise within the measurement channel to its uppermost position when the channel is substantially completely filled with fluid. At such point the closure of an appropriate valve prevents the entry of further fluid from the main conduit into the measurement channel so that substantially all of the fluid which is now diverted from the main stream flows into the second, or auxiliary, channel of the secondary conduit system. Such fluid passes by the angularly disposed screen at the entrance to the measurement channel and, as it does so, it carries away substantially all of the material which previously has been collected on the screen so as to clean the screen in an extremely effective manner. The removed material is carried through the second channel of the secondary conduit system back into the main stream. Accordingly, the removal of material from the screen represents, in effect, a "self-cleaning" operation and disassembly of the device for such purpose is avoided.

Although fluid flow in the measurement channel stops when the measurement is made, fluid continues to flow in the second channel so that the housing within which both channels are formed is effectively maintained at the temperature of the fluid being measured. Maintenance of the housing temperature at the desired level tends to keep the fluid in the measurement channel at the required level for providing an accurate viscosity determination.

In addition, an external visual indication of the position of the free-falling piston in the measurement channel is also provided. For such purpose a portion of the piston assembly is formed of magnetic material. An external body of magnetic material is placed in an exterior groove on the outer surface of the measurement channel housing structure. The magnetic materials are of opposite polarities so that, as the piston (and its magnetic portion) moves upwardly and downwardly within the channel, the external magnetic body in the exterior groove also moves in a corresponding manner. The groove is sufficiently long so that when the piston reaches the desired uppermost and lowermost positions within the channel, the externally visible magnet indicator is in its uppermost and lowermost positions in the groove so that the operator knows whether the free-fall measurements have begun and ended at the correct positions.

Further, it is desirable that the flow of fluid into the measurement channel be adjusted to assure adequate operation of the device. For this purpose a second piston assembly can be placed within the second channel of the secondary conduit system, such piston also having a magnetic portion as a part thereof. In a similar manner, an external magnet can also be placed within a groove on the exterior of the second channel housing so that the position of the internal piston can also be visually indicated thereby. The flow in the second channel is adjusted, as by a throttle valve, for example, so that the portion of the main stream which is diverted into the second channel has a flow velocity which is just strong enough to raise the piston to the top of the second channel, thereby providing an indication that sufficient fluid flow is present from the main stream to permit suitable operation of the measurement piston in the measurement channel. Thus, the second channel of the secondary conduit system provides a means for cleaning the screen, as well as a means assuring that the fluid temperature is at its desired level for measurement and for producing a visual indication of the fluid flow adjustment characteristics as are needed to provide suitable operation of the overall measurement device.

DESCRIPTION OF THE INVENTION

Figure 3:
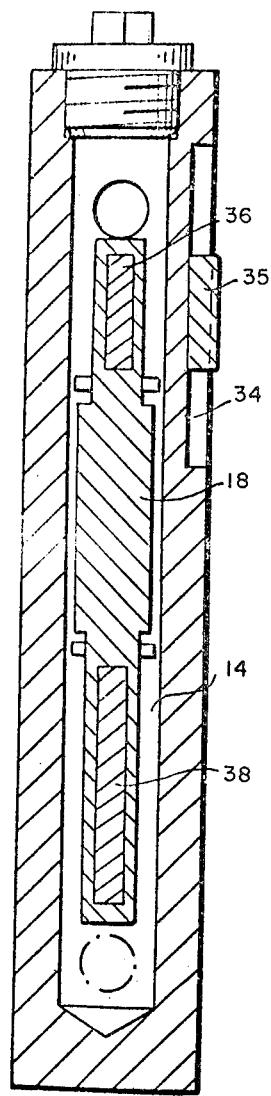
Figure 4:
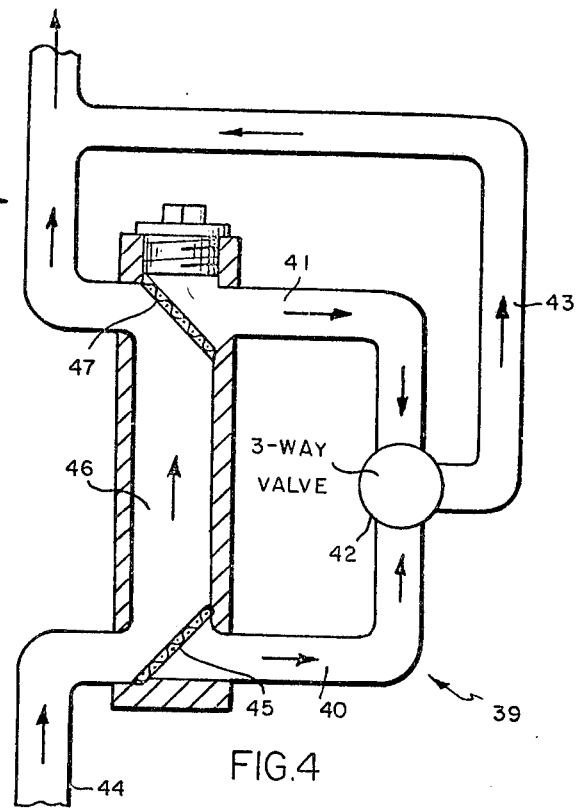
Figure 2:
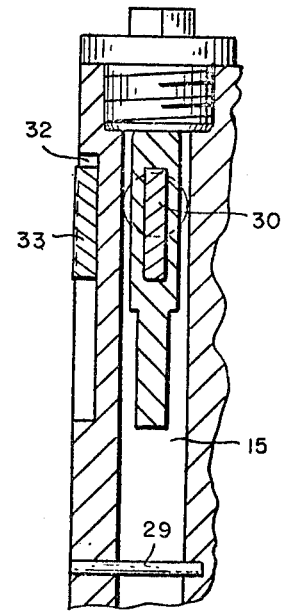

The invention can be described in more detail with the help of the accompanying drawing wherein:

FIG. 1 shows a sectional view of a preferred embodiment of the invention;

FIGS. 2 and 3 show other sectional views of the preferred embodiment of the invention taken along the lines 2—2 and 3—3, respectively, of FIG. 1; and FIG. 4 shows a diagrammatic view of an alternative embodiment of the invention.

As can be seen in FIG. 1, a fluid 12, such as a liquid, whose viscosity is to be measured, flows through a main conduit 10, shown diagrammatically, in the exemplary direction shown by the arrows 11. A portion of the fluid 12 can be diverted from the main conduit into a secondary conduit system 13 which includes a first channel 14 and a second channel 15 supplied from a common line 16 through a suitable valve 17 which can be placed in an on or an off position to provide such diversion or not, as desired. Such a system may be utilized for measuring the viscosity of the fluid 12 flowing in main conduit 10, channel 14 being utilized for such viscosity measurement. Such measurement can be made in the manner discussed in the above-referenced U.S. Pat. No. 3,686,931 and has a piston 18 freely removable in a vertical direction therein.

When a measurement is to be made the fluid which is diverted into channel 14 and which normally flows outwardly therefrom as shown by arrow 19 is prevented from further flow by the closing of a valve 20 which thereby traps fluid within channel 14, such fluid then being at a rest position. Because of the entry of fluid flow into channel 14 when valve 20 is open (the fluid thereupon flowing through line 21 and eventually back into the main conduit 10), piston 18 is forced upwardly by the fluid flow pressure to its uppermost position within the channel. When valve 20 is closed, the fluid flow stops and the pressure which retains piston 18 at its upper position is removed and the piston is caused to freely fall through the fluid by gravity to its lowermost position. The time of fall over a predetermined distance provides a measurement of the viscosity, as is well known from the disclosure of the above-referenced patents. In presently available devices the piston is assumed to be at its uppermost position when the valve 20 is closed. The point in time at which the valve is closed until the point in time when the piston reaches its lowermost position must be determined. The latter point in time can be determined by an appropriate proximity switching circuit 37 which operates magnetically, as discussed in above-referenced U.S. Pat. No. 3,677,070. A magnet portion 38, which is formed as part of the piston assembly within channel 14, is provided for such purpose as discussed in the aforesaid patent.

In accordance with the embodiment of the invention in FIG. 1, as fluid is conveyed to channel 14 from the diverted fluid stream in portion 16 of second conduit system 13, it passes through a filter means in the form of a wire mesh screen 22 which is angularly disposed with respect to the entrance of channel 14. Any particles larger than the mesh dimensions are prevented from entry into channel 14 and are generally retained against the screen by the fluid flow pressure which is present. For example, in a preferred embodiment it has been found that the angle can conveniently be set at about 45°, as shown in FIG. 1, although the angle need not be limited to such value.

When valve 20 is closed so that no further fluid is permitted to enter channel 14, substantially all of the fluid entering conduit portion 16 is thereupon caused to flow upwardly through channel 15, which is arranged substantially parallel to channel 14, as shown. As the diverted stream passes by screen 22 it removes the particles which have been retained on the screen during the entry of fluid therethrough into channel 14. The removed particles are thereupon carried along with the fluid through channel 15 and ultimately back into the main stream 12 as shown by arrows 23.

Such action thereby provides for a substantially complete cleaning of screen 22 without the necessity for dismantling the device in order to obtain access to the screen for cleaning or replacement thereof. Accordingly, the fluid in channel 14 always remains substantially clear of undesired particles, at lease of a size above the mesh size of the screen, the latter being suitably selected for the particular fluid which is being handled. It is, of course, within the skill of those in the art to design the apparatus so that it can be suitably disassembled to permit physical access to screen 22 so that it can be removed for inspection and further cleaning or so that a replacement screen can be substituted therefor.

As mentioned above, when the fluid flow is stopped in channel 14 for the measurement to take place, in previously designed apparatus of this type the temperature of the fluid tends to change during the measurement time period if the fluid temperature is other than at room temperature. Since fluid viscosities vary with temperature and since such apparatus, for example, is often used to measure viscosities at relatively high temperatures, changes in temperature during the measurement time period will adversely affect the accuracy of the viscosity measurement.

In the apparatus of the invention as described herein, however, such a problem is avoided. Since the fluid from main conduit 10 continues to flow through channel 15 during the measurement time period, the temperature of the metal housing within which both channels 14 and 15 are formed tends to remain at the same temperature as the fluid. Accordingly, the fluid within channel 14 tends to be kept at a relatively constant level substantially equal to the level of the temperature of the fluid in main conduit 10 and the desired accuracy of the viscosity measurement is assured.

It is desirable to assure that sufficient fluid pressure is provided in the measurement channel 14 to raise the piston 18 to its desired uppermost position and also to assure that excessive pressure is not present which would cause the piston to rise too rapidly and, perhaps, cause damage thereto. In order to control such pressure, a throttle valve 24 is positioned adjacent a shut-off valve 25 in the output line 26 of the secondary conduit system 13 which carries fluid back into the main stream of primary conduit 10. In order to assure that the throttle valve is appropriately adjusted for the desired fluid flow pressure channel 15 has positioned therein a piston assembly 27 which freely moves therein from a stop, or lower limit, position 28, at which a stop pin 29 is located to an uppermost position at the top of channel 15 (the position shown in FIG. 1). Piston assembly 27 has a diameter suitably selected for the fluid which is being measured, as discussed below. A portion of the piston assembly includes an upper member 30 which has imbedded therein a magnet 31. When the flow rate of the main stream through channel 15 is adjusted by throttle valve 24 so that piston assembly 27 just reaches its uppermost position for retention thereat by the fluid flow pressure, the flow rate has been adjusted to the correct level. Such flow rate is acceptable for permitting flow into channel 14 so as to raise piston 18 while, at the same time, the flow rate is not so high as to raise the latter piston too rapidly.

In order for an operator to determine that such condition exists, a visual indication of the position of piston 27 in channel 15 is required, since such piston will not be externally visible through the channel housing. In order to provide such indication, as best shown in the view of FIG. 2, a groove 32 is formed in the exterior surface of the housing which forms channel 15 and a freely moving magnet 33 is placed within such groove. The polarities of magnets 30 and 33 are oppositely oriented so that, as magnet 30 moves upwardly and downwardly within channel 15, magnet 33 moves correspondingly within groove 32. Thus, when external magnet 33 just reaches, and is held at, its uppermost position in groove 32, the operator knows that the throttle valve 24 is correctly adjusted. Under such conditions the flow rate of the diverted main stream in secondary conduit system 12 is correctly adjusted for operation of the measurement piston 18 in channel 14.

It is desirable also to know the position of piston 18 within channel 14, and, accordingly, for such purpose an external groove 34 is also provided in the exterior surface of the housing for channel 14 (in the same manner as groove 32 in channel 15) as best shown in FIG. 3. A freely movable magnet 35 is placed within the groove 34, the upper portion of the piston assembly 18 in channel 14 also having a magnet 36 imbedded therein. The polarities of magnets 35 and 36 are oppositely oriented so that they are attracted and, thus, as piston assembly 18 moves within channel 14, the external magnet 35 moves in a corresponding manner to provide an indication of the position of piston 18. Since an external indication of the position of piston assembly 18 is available, the time measurement required in determining viscosity need not be made from the point in time when valve 20 is closed to the point in time when an external proximity switch is actuated, as discussed above. It is now possible to place appropriate markings on the exterior of the housing for channel 14 so that the time period of the travel of a selected point on magnet 35 from one marking to another can be used as the required time period for making the viscosity determination. Such measurement should provide greater accuracy than in previous devices since it has been found that reliable accuracy of the time is not always achieved when using the uppermost and lowermost end point positions for such time measurement.

In summary, the apparatus as shown in FIGS. 1 to 3, first of all, provides for a clear stream of fluid for use in making the measurement in channel 14, a self-cleaning screen arrangement being arranged for avoiding the need for disassembly of the device in order to clean the particles which are removed by the screen. Further, an appropriate visual indication of an auxiliary piston is provided for permitting the correct setting of the fluid flow rate for measurement purposes. In addition, a visual indication of the position of the measurement piston is also provided so that the need for a proximity switch, as in previous devices of this type, can be avoided and a cost savings can be achieved.

While a portion of the fluid in main conduit 10 is shown in FIG. 1 as being diverted into secondary conduit 13 where it flows through channels 14 and 15 and thence back into the main conduit, the apparatus may also be arranged so that channel 15 effectively acts as the main conduit itself (in a manner similar to that shown in FIG. 4, described below).

While the concept for providing a self-cleaning screen has proved useful for viscometers, such concept can also be used in any structure which may require a sampling of a main fluid stream in a side stream for measurement or other purposes. In some cases, the side, or sampling, stream may require a continuously flowing stream of fluid rather than the intermittently flowing stream, discussed in the viscometer device of FIGS. 1 to 3. For the continuous flow case a system of the type shown in FIG. 4 can be used. As seen therein, the secondary conduit system 39 includes a pair of side channels 40 and 41 which supply fluid to a three-way valve 42, the output of which is continuously supplied to an output line 43 from either channel 40 or 41. Channel 43 can be used as a measurement channel, the sampled fluid returning directly to the main stream therefrom.

When three-way valve 42 is in a first position so as to supply fluid only from channel 40 therethrough to channel 43, fluid which has been diverted from the main conduit 44 is fed into channel 40 via screen member 45 which is positioned at an appropriate angle, such as 45° at the entrance to channel 40. As the fluid is supplied into channel 40, any particles which are filtered out by the screen are retained against the screen 45 so that none of such material enters channel 40.

After a preselected time period, for example, the three-way valve 42 is placed in its second position wherein fluid is supplied to channel 43 only via channel 41. In such case the diverted fluid stream from main conduit 44 is carried through a channel 46 and enters channel 41 via a second screen 47 placed at a selected angle, such as 45°, with reference to the entrance to channel 41. As such stream passes by screen 45, the material which has previously been retained thereon is carried away by the stream flowing into channel 46. Such material is ultimately carried back into the main fluid stream in conduit 44. During such operation material in the fluid entering channel 41 is prevented from such entry by screen 47 and is retained thereat.

When valve 42 is subsequently returned to its first position after a preselected time period, the main stream from conduit 44 again enters channel 40, while the portion of the main stream which flows through channel 46 passes by screen 47 and removes the material that had previously been retained thereon.

In such a manner, each of the screens is alternately cleaned and a continuous flow of clear fluid is provided in the output measurement channel 43.

In order to provide for the necessary fluid flow in output channel 43, it may be helpful, or necessary, to produce a pressure drop in channel 46. Such a pressure drop can be produced, for example, by providing a restriction (e.g., a restrictive orifice or a reduction in conduit diameter) at a location shown by arrow 48 just before the fluid flow in channel 46 joins that in channel 43 to return to the main stream.

While the above described embodiments represent preferred embodiments of the invention, other embodiments and modifications thereof within the spirit and scope of the invention may occur to those in the art. Hence, the invention is not to be considered as limited to the specific embodiments shown and described herein except as defined by the appended claims.

What is claimed is:

1. A fluid handling system comprising
a main conduit system;
a secondary conduit system comprising a first channel and a second channel;
means for diverting at least a portion of the fluid flowing in said main conduit system into said secondary conduit system;
filter means positioned at the entrance to said first channel for permitting fluid to flow into said first channel and for preventing the entry of material above a predetermined size, said material generally being retained at said filter means;
valve means permitting fluid to flow into said first channel when open and preventing further flow of said fluid into said first channel when closed, substantially all of the fluid diverted from said main conduit flowing through said second channel and passing by said filter means when said valve means is closed, the passage of said fluid by said filter means thereby removing substantially all of the material previously retained thereat; and
means for returning said fluid and said removed material to said main conduit system.

2. A system in accordance with claim 1 wherein said filter means is a wire mesh screen.

3. A system in accordance with claim 2 wherein said screen is positioned at a selected angle with respect to the plane of entry of said first channel.

4. A system in accordance with claim 3 for measuring a selected characteristic of said fluid wherein said first channel includes
means for measuring said selected characteristic during the time period when the further flow of fluid into said first channel has been prevented, the removal of said material from said filter means occurring during said measurement time period.

5. A system in accordance with claim 4 wherein said valve means is actuated to permit said fluid flow into said first channel and to prevent said fluid flow into said first channel in a periodic manner.

6. A system in accordance with claim 4 wherein said measuring means comprises means for measuring the viscosity of said fluid.

7. A system in accordance with claim 6 wherein said viscosity measuring means includes piston means capable of freely moving through the fluid in said first channel, the time period over which said piston moves downwardly through a preselected distance through said fluid at rest in said first channel providing an indication of the viscosity of said fluid.

8. A system in accordance with claim 7 and further including means external to said first channel for determining when said piston reaches a position at the end of said preselected distance.

9. A system in accordance with claim 8 wherein said external means comprises a proximity detection means for detecting the presence of said piston when it reaches the end of said preselected distance and means responsive to said detection for providing a visual indication thereof.

10. A system in accordance with claim 9 wherein said detection is achieved by magnetic coupling means.

11. A system in accordance with claim 7 wherein said piston means is caused to move upwardly within said first channel when said fluid is permitted to flow therein and is caused to move downwardly by gravity when the flow of fluid into said first channel is prevented and said fluid is at rest therein.

12. A system in accordance with claim 11 wherein
said piston means includes a first magnet means; and said system further includes
a second magnet means mounted in a freely movable manner adjacent but external to said first channel so that movement of said piston means within said first channel causes a corresponding movement of said second magnet means external to said first channel, whereby a visual indication of the position of said piston means in said first channel is provided.

13. A system in accordance with claim 12 wherein said second channel includes a second piston means freely movable through the fluid therein, said second piston means being movable upwardly within said second channel when fluid flows therein.

14. A system in accordance with claim 13 wherein
said second piston means includes a third magnet means; and said system further includes
a fourth magnet means mounted in a freely movable manner adjacent but external to said second channel, so that movement of said second piston means within said second channel causes a corresponding movement of said fourth magnet means external to said second channel, whereby said fourth magnet means provides a visual indication of the position of said second piston means in said second channel.

15. A system in accordance with claim 14 and further including adjustable valve means for controlling the flow of said diverted fluid in said second conduit means, said flow being capable of adjustment so as to permit the flow thereof in said second channel to move said piston upwardly to the top of said channel as indicated by said second external magnet means.

16. A fluid handling system comprising
a main conduit means having a fluid flowing therein;
a secondary conduit means;
means for diverting at least a portion of the fluid flowing in said main conduit means into said secondary conduit means,
said secondary conduit means comprising a first channel,
a second channel comprising a common line and first and second auxiliary lines, each capable of supplying fluid to said first channel;
valve means for alternately connecting the output from each of said auxiliary lines to said first channel whereby fluid is supplied in a substantially continuous manner thereto;
first filter means positioned at the entrance to said first auxiliary line for preventing the entry of material above a predetermined size into said first auxiliary line, said material generally being retained at said first filter means;
second filter means positioned at the entrance to said second auxiliary line for preventing the entry of material above said predetermined size into said second auxiliary line, said material generally being retained at said second filter means;
whereby the flow of fluid past said second filter means when said valve means supplies fluid to said first channel from said first auxiliary line thereby removes the material that has been retained at said second filter means and the flow of fluid past said first filter means when said valve means supplies fluid to said first channel from said second auxiliary line thereby removes material from said first filter means; and
means for returning said fluid and said removed material from each of said first and second filter means to said main conduit means.

* * * * *